US005239117A

United States Patent [19]

Nicholas et al.

[11] Patent Number: 5,239,117

[45] Date of Patent: Aug. 24, 1993

[54] RHODIUM CATALYZED HYDROGEN TRANSFER REDOX REACTIONS

[75] Inventors: Kenneth M. Nicholas; Jing-Cherng Tsai, both of Norman, Okla.

[73] Assignee: Board of Regents of the University of Oklahoma, Norman, Okla.

[21] Appl. No.: 761,608

[22] Filed: Sep. 18, 1991

[51] Int. Cl.$^5$ .............. C07C 53/02

[52] U.S. Cl. .............. 562/609

[58] Field of Search .............. 502/166; 562/609; 423/230

[56] References Cited

U.S. PATENT DOCUMENTS

| | | | |
|---|---|---|---|
| 3,511,885 | 5/1970 | Hughes | 502/166 |
| 3,743,664 | 7/1973 | Franco et al. | 502/166 |
| 4,578,523 | 3/1986 | Bahrmann et al. | 502/166 |
| 4,855,496 | 8/1989 | Anderson et al. | 562/609 |

FOREIGN PATENT DOCUMENTS

| | | | |
|---|---|---|---|
| 56-166146 | 12/1981 | Japan | 502/166 |

OTHER PUBLICATIONS

Hirai, Nutton & Maitlis, "Pentamethylcyclopentadienyl-Rhodium and -Iridium Complexes". Part 27. Catalysed Oxygenation Reactions; . . . (1981).

Inoue, Isumida, Sasaki & Hashimoto, "Catalytic Fixation of Carbon Dioxide to Formic Acid by Transition-Metal Complexes Under . . ." (1976).

Schrock & Osborn, "Rhodium Catalysts for the Homogeneous Hydrogenation of Ketones", Chemical Communications (1970) pp. 567-568.

Hashimoto, Harukichi, Inoue, Yoshio, "Formic Acid and its Esters", Chemical Abstracts, vol. 87 (1977) p. 498.

Hashimoto, Shunkichi, Inoue, Yoshio, "Formic Acid and its Esters", Chemical Abstracts, vol. 88 (1978) p. 555.

*Primary Examiner*—Michael Lewis

*Assistant Examiner*—Stuart L. Hendrickson

*Attorney, Agent, or Firm*—Dunlap, Codding & Lee

[57] ABSTRACT

Oxidation/reduction processes catalyzed by soluble rhodium complexes of the type $(L_{4 or 5}Rh)Z^-$ wherein each L is selected from a group consisting essentially of monophosphines, diphosphines, olefins and coordinating solvents with the proviso that at least one L is a phosphine and Z is a weakly coordinating anion. In one embodiment, formic acid is produced by the hydrogenation of carbon dioxide. In another embodiment oxygen/carbon dioxide mixtures are used to oxidize organic compounds (ethers, amines, olefins) with coproduction of formic acid. In a third embodiment, these organic compounds are selectively oxidized by oxygen alone, without the coproduction of formic acid.

19 Claims, No Drawings

RHODIUM CATALYZED HYDROGEN TRANSFER REDOX REACTIONS

FIELD OF THE INVENTION

The present invention comprises selective catalytic redox reactions utilizing a cationic rhodium complex.

SUMMARY OF THE INVENTION

Currently the search for selective and efficient catalytic redox reactions is one of the most sought after objectives in the field of chemical synthesis and technology. Typically, catalytic oxidations of organic compounds, especially those with molecular oxygen as the oxidant, are often plagued by poor product selectivity, reflecting their typical free radical character and excessive exothermicities.

Carbon dioxide is an attractive feed stock for organic chemicals because it is the world's most abundant carbon resource. Moreover, the buildup of excess carbon dioxide and the associated greenhouse effect is currently believed to be a serious threat to the environment. However, the use of carbon dioxide has been limited due to its perceived inertness (hyporeactivity).

This invention discloses a catalytic process which significantly impacts the above mentioned areas of chemical technology as well as others which will be apparent to one skilled in the art upon a consideration of the specification and claims herein.

DETAILED DESCRIPTION OF THE PREFERRED EMBODIMENTS

The Catalyst

This invention utilizes cationic rhodium complexes to catalyze reactions. The rhodium complex has the general formula:

$$(L_{4 or 5}Rh)^{+}Z^{-}$$

wherein each L is selected from a group consisting essentially of monophosphines, diphosphines, olefins and coordinating solvents wherein at least one L is a phosphine.

Examples of suitable coordinating solvents include nitriles, amines, ketones, and ethers. $Z^-$ is preferably a weakly coordinating anion such as $BF_4^-$, $PF_6^-$, $BPh_4$, and $ClO_4^-$.

In a preferred embodiment for the catalyst the rhodium complex may be designated by the formula:

$$[L'_{5-(X+Y)}Rh(olefin)_X S_Y]^{+}Z^{-}$$

In this formula X or Y may be any integer from 0 to 4 with the proviso that X+Y may not exceed 4. Each L' is selected from monophosphines or diphosphines and S is a coordinating solvent such as is described above. Preferably when 5−(X+Y) is 1, each L' is selected from diphosphines with a general formula $R_2P(CH_2)_ZPR_2$. When 5−(X+Y) is 3, or 4, each L' is preferably selected from monophosphines with the general formula $R_3P$, and when 5−(X+Y) is 2, each L' is preferably selected from monophosphines and diphosphines having the general formulas set forth above. In these formulas $R_3$ is preferably a group of three R's (the same or different) wherein each R is an alkyl or an aryl. Similarly, $R_2$ is a group of two R's. (the same or different) wherein each R is preferably an alkyl or an aryl. The olefin or olefins are preferably selected from monoenes and dienes when X is 1 or 2 and from monoenes when X is 3 or 4, and $Z^-$ is a weakly coordinating anion such as described above.

FIRST EMBODIMENT

Formic acid is a valuable product in itself and as a chemical intermediate. Formic acid is presently manufactured mainly as a byproduct in the liquid phase oxidation of hydrocarbons to acetic acid or by the hydration of carbon monoxide. While the catalytic hydrogenation of carbon dioxide to formic acid has been reported, these reactions required the addition of promoters such as water or basic additives and the activities of these prior art methods are low even at elevated temperatures.

In this embodiment, when the rhodium complex is combined with carbon dioxide gas, hydrogen gas and an organic solvent, a reaction will occur wherein formic acid is produced, as may be represented by equation A below.

$$H_2+CO_2 \rightarrow HCO_2H \quad (A)$$

In this way, carbon dioxide is consumed and efficiently reduced to produce formic acid using hydrogen gas as reductant in the presence of the rhodium catalyst. The organic solvent is preferably a polar solvent that will not enter into the reaction, suitable solvents include ethers, ketones, nitriles, esters, amides and carboxylic acids.

The pressure of the carbon dioxide gas is preferably from about 1 to 50 atmospheres and more preferably at least 25 atmospheres. The pressure of the hydrogen gas is preferably from about 1 to 100 atmospheres and more preferably at least 50 atmospheres.

Advantageously, the reaction may be carried out at in a wide temperature range, but a temperature within the range of 0° to 150° centigrade ("C") is recommended and more preferably from 30° to 50° C. Since this reaction is thermodynamically limited, maximum conversion to formic acid is best obtained at lower temperatures, such as near room temperature. Higher temperatures lead to higher reaction rates, but lower conversion to formic acid; that is, higher temperatures increase the rate of reaction, but decrease the percentage of carbon dioxide converted.

Although not required for the reaction to occur, the addition of small amounts (0.05–0.10%) of water does accelerate the rate of formic acid production.

It should be noted that conversions to formic acid are much higher in equation B, discussed in detail below, than in equation A because of the greater thermodynamic driving force derived from using oxygen as a co-reactant.

SECOND EMBODIMENT

As illustrated in this embodiment the invention discloses a process which simultaneously mediates the non-selective, hyperreactivity of molecular oxygen and enhances the activity of "hyporeactive" carbon dioxide. When this invention is used with molecular oxygen and carbon dioxide in the same reaction, the carbon dioxide is reduced to formic acid while producing valuable oxidized organic compounds from relatively inexpensive organic compounds. For example, an ether may be converted to an ester or a lactone, or an amine may be converted to an amide while carbon dioxide is consumed and reduced to the amine formate salt. In this embodiment the reaction may be represented by equation B below.

$$SubH_2+O_2+CO_2\rightarrow SubO+HCO_2H \quad (B)$$

Oxidations of ethers to lactones and esters have been carried out in a variety of ways, all of which have disadvantages when compared to this invention. For example, esters may be oxidized stoichiometrically with $RuO_4$, which is prohibitively expensive for all but very small scale reactions, or catalytically in the presence of Ru complexes with relatively costly hypochlorite or periodate as oxidants, or with variable product selectivity using $Pt/O_2$.

Prior catalytic reactions of these substrates with oxygen have often been unselective, especially in the case of olefins, producing complex mixtures and over oxidation. The selective oxidation of N-substituted pyrrolidines to the corresponding pyrrolidones with this invention is especially noteworthy since tertiary amines typically are oxidized to amine oxides with most oxidants. Furthermore, with this invention, the oxidations employing carbon dioxide as a co-reactant produce formic acid as a valuable co-product.

In this embodiment when the rhodium complex is combined with carbon dioxide gas, oxygen gas and an organic compound, a reaction will occur wherein formic acid and an oxidized organic compound are produced If the organic compound is a solid or a gas, it should be dissolved in an organic solvent and preferably an inert organic solvent, i.e. one which will not enter into the reaction. In this embodiment the solvent is preferably selected from halogenated hydrocarbons, esters, amides or carboxylic acids.

The organic compound may be in a liquid form itself In that case, it is not necessary to add another liquid to act as a solvent. For example, combining the solvent tetrahydrofuran (THF) and carbon dioxide gas at 50 atmospheres pressure with $[(NBD)Rh(PMe_2Ph)_3]BF_4$ (1) produces formic acid and an equal molar amount of 2-butyrolactone (turnover #4 mol/mol 1/day at 20° C.), the apparent oxidation product of the THF solvent. It is not clear whether carbon dioxide is the source of the new oxygen introduced in forming the lactone, but when $O_2/CO_2$ mixtures are used, the coproduction of lactone and formic acid occurs at an accelerated rate (TN ca. 10 mol/mol 2/day) at much lower pressures (1-10 atm). Isotopic labeling experiments under these conditions using $^{18}O_2$ and $^2$H-THF, have revealed that the lactone oxygen is derived from molecular oxygen and the THF supplies the hydrogen for formic acid production. Thus, the rhodium complex functions as a hydrogen transfer catalyst, oxygen is the stoichiometric oxidant, and carbon dioxide serves as the hydrogen reservoir.

Advantageously, the pressure of the carbon dioxide gas preferably is from about 1 to 50 atmospheres, and the pressure of the oxygen gas is preferably from about 1 to 100 atmospheres and more preferably from 1 to 10 atmospheres. In addition, the reaction may be carried out at in a wide temperature range, but a temperature within the range of 0° to 150° centigrade is recommended.

Other ethers, both cyclic and acyclic are similarly converted to lactones or esters respectively with coproduction of formic acid. For example, ethyl ether is converted to ethyl acetate and formic acid (T=100° C., 3 atm $O_2$, 20 atm $CO_2$; ca. 3 turnovers/hr). Similarly, tertiary amines may be converted to amides under similar conditions with co-production of the corresponding ammonium formates. For example, N-methylpyrrolidine is oxidized to N-methylpyrrolidone.

THIRD EMBODIMENT

In addition, one may use this invention to promote the selective oxidations of organic compounds without the co-production of formic acid. For example, compounds such as ethers and olefins may be oxidized to their corresponding α-hydroperoxides and tertiary amines may be oxidized to amides. For a more specific example, tetrahydrofuran (THF) is transformed to 2-hydroperoxytetrahydrofuran (ca. 10 turnovers/hr) and cyclohexene is converted to 3-hydroperoxycyclohexene (ca. 30 turnovers/hr) along with a small amount (ca. 10%) of cyclohexenone. Under similar conditions, tertiary amines are oxidized to amides. Thus, N-methyl pyrrolidine is oxidized selectively to N-methyl pyrrolidone (60 ° C., ca. 10 turnovers/hr). With this embodiment the reaction may be represented by equations C and C' below.

$$R{-}H+O_2\rightarrow R{-}OOH$$

$$R_2N{-}CH_2R'+O_2\rightarrow R_2N{-}C(O)R'$$

In this embodiment, when the rhodium complex is combined with oxygen gas and an organic compound, a reaction will occur wherein an oxidized organic compound is produced. For example, an alkylaromatic compound will be converted into its corresponding α-hydroperoxide.

If the organic compound is a solid or a gas, it should be dissolved in an organic solvent and preferably an inert organic solvent. An inert organic solvent is any organic solvent which 10 will not enter into the reaction. For example, in this embodiment if the organic compound is an ether or olefin, then the solvent is preferably selected from solvents drawn from the category of aryl halide, amide, ester, or nitrile. The organic compound may be in a liquid form itself, and in that case, there is no need to add another liquid to act as a solvent.

In this embodiment the pressure of the oxygen gas is preferably from 1 to 10 atmospheres and the reaction is preferably carried out in the temperature range of 0° to 150° C. The following examples illustrate the practice of the present invention.

EXAMPLE 1

A stainless steel autoclave containing 0.05 g of $Rh(PMe_2Ph)_3$(norbornadiene)$BF_4$, 50 mL of tetrahydrofuran and 0.2 mL of water was charged first with 700 psi $H_2$ and then with 700 psi $CO_2$ and then stirred magnetically at 20° C. for 3 days. After depressurizing, IR analysis indicated the production of formic acid (130 mol/mol Rh). Addition of pentane (to precipitate Rh salts) and fractional distillation provided pure formic acid.

EXAMPLE 2

A solution of 0.05 g $Rh(PMe_2Ph)_3$(norbornadiene)$BF_4$ in 50 mL of tetrahydrofuran was stirred under 15 psi $O_2$ and 15 psi $CO_2$ at 20° C. After 8 days GC/MS and IR analysis indicated the formation of γ-butyrolactone (80 mol/mol Rh) and formic acid (85 mol/mol Rh).

EXAMPLE 3

A suspension of 0.05 g $Rh(PMe_2Ph)_3$(norbornadiene)$BF_4$ in 50 mL of diethyl ether in a stainless steel autoclave was pressurized with 50 psi $O_2$ and 300 psi $CO_2$ and then was heated to 100° C. for 12 hours. Following cooling and depressurization, GC/MS and IR analysis indicated the formation of ethyl acetate (30 mol/mol Rh) and formic acid (30 mol/mol Rh).

EXAMPLE 4

A solution of 0.05 g $Rh(PMe_2Ph)_3$(norbornadiene)$BF_4$ in 20 mL of N-methylpyrrolidine was stirred under 15 psi $O_2$ at 60° C. for 12 hours. After cooling of the mixture, GC/MS and IR analysis indicated the formation of N-methylpyrrolidone (130 mol/mol Rh) which was isolated by distillation.

EXAMPLE 5

A solution of 0.05 g $Rh(PMe_2Ph)_3$(norbornadiene)$BF_4$ in 15 mL of cyclohexene was stirred under 15 psi $O_2$ at 80° C. for 6 hours. After cooling of the mixture, evaporation of excess cyclohexene left a 12:1 mixture of cyclohexenyl hydroperoxide and cyclohexenone (330 mol/mol Rh) when analyzed by $^1H$ NMR.

Changes may be made in the embodiments of the invention described herein or in parts or elements of the embodiments described herein or in the steps or in the sequence of steps of the methods described herein without departing from the spirit and scope of the invention as defined in the following claims.

What is claimed is:

1. A process for reducing carbon dioxide to formic acid consisting essentially of:

combining ingredients consisting of an organic solvent, carbon dioxide gas and hydrogen gas in the presence of a rhodium complex at a temperature in the range of about 0° to 150° C., wherein the rhodium complex has the general formula;

$$(L_{4\ or\ 5}Rh)^+Z^-$$

wherein:

each L is selected from a group consisting of monophoshines, diphosphines, olefins, and coordinating solvents with the proviso that at least one L is a phosphine; and Z is a weakly coordinating anion selected from a group consisting of $BF_4^-$, $PF_6^-$, $BPh_4^-$, and $ClO_4^-$.

2. The process of claim 1 wherein:

the monophosphines have the general formula $R_3P$ wherein $R_3$ is a group of three R's and each R is an alkyl or an aryl; and the diphosphines have the general formula $R_2P(CH2)_zPR_2$ wherein $R_2$ is a group of two R's and each R is an alkyl or an aryl.

3. The process of claim 1 wherein the organic solvent is selected from a group consisting of ethers, ketones, nitriles, esters, amides, and carboxylic acids.

4. The process of claim 1 wherein the pressure of the carbon dioxide gas is from about 1 to 50 atmospheres, and the pressure of the hydrogen gas is from about 1 to 100 atmospheres.

5. The process of claim 1 wherein the pressure of the carbon dioxide gas is at least 25 atmospheres.

6. The process of claim 1 wherein the pressure of the hydrogen gas is at least 50 atmospheres.

7. The process of claim 1 wherein the combination of carbon dioxide gas, hydrogen gas and rhodium complex is at a temperature in the range of about 30° to 50° C.

8. A process for the co-production of formic acid and oxidized organic compounds consisting essentially of:

combining ingredients consisting of carbon dioxide gas, oxygen gas and an organic compound in the presence of a rhodium complex at a temperature in the range of about 0° to 150° C., wherein the rhodium complex has the general formula:

$$(L_{4\ or\ 5}Rh)^{30}Z^-$$

wherein:

each L is selected from a group consisting of monophosphines, diphosphines, olefins, and coordinating solvents with the proviso that at least one L is a phosphine; and Z is a weakly coordinating anion selected from a group consisting of; $BF_4^-$, $PF_6^-$, $BPh_4^-$, and $ClO_4^-$.

9. The process of claim 8 wherein the organic compound is dissolved in an organic solvent.

10. The process of claim 9 wherein the organic solvent is selected from the group consisting of halogenated hydrocarbons, esters, amides, and carboxylic acids.

11. The process of claim 8 wherein the pressure of the carbon dioxide gas is from about 1 to 50 atmospheres and the pressure of the oxygen gas is from about 1 to 100 atmospheres.

12. The process of claim 8 wherein the pressure of the oxygen gas is about 1 to 10 atmospheres.

13. A process for reducing carbon dioxide to formic acid consisting essentially of:

combining ingredients consisting of water, an organic solvent, carbon dioxide gas and hydrogen gas in the presence of a rhodium complex at a temperature in the range of about 0° to 150° C., wherein the rhodium complex has the general formula;

$$(L_{4\ or\ 5}Rh)^+Z^-$$

wherein:

each L is selected from a group consisting of monophosphines, diphosphines, olefins, and coordinating solvents with the proviso that at least one L is a phosphine; and Z is a weakly coordinating anion selected from a group consisting of; $BF_4^-$, $PF_6^-$, $BPh_4^-$, and $ClO_4^-$.

14. The process of claim 13 wherein:

the monophosphines have the general formula $R_3P$ wherein $R_3$ is a group of three R's and each R is an alkyl or an aryl; and the diphosphines have the general formula $R_2P(CH2)_zPR_2$ wherein $R_2$ is a group of two R's and each R is an alkyl or an aryl.

15. The process of claim 13 wherein the organic solvent is selected from the group consisting of ethers, ketones, nitriles, esters, amides, and carboxylic acids.

16. The process of claim 13 wherein the pressure of the carbon dioxide gas is from about 1 to 50 atmospheres, and the pressure of the hydrogen gas is from about 1 to 100 atmospheres.

17. The process of claim 13 wherein the pressure of the carbon dioxide gas is at least 25 atmospheres.

18. The process of claim 13 wherein the pressure of the hydrogen gas is at least 50 atmospheres.

19. The process of claim 13 wherein the combination of carbon dioxide gas, hydrogen gas and rhodium complex is at a temperature in the range of about 30° to 50° C.

* * * * *

UNITED STATES PATENT AND TRADEMARK OFFICE

CERTIFICATE OF CORRECTION

PATENT NO. : 5,239,117

DATED : August 24, 1993

INVENTOR(S) : Kenneth M. Nicholas, et al.

It is certified that error appear : in the above-indentified patent and that said Letters Patent is hereby corrected as shown below:

On the title page, item: [57] Abstract, line 2; after type, please delete "$(L_{4\ or\ 5}Rh)Z^-$" and substitute therefor --$(L_{4\ or\ 5}Rh)^+Z^-$--.

Column 2, Line 35, after carried out, please delete "at".

Column 3, Line 29; after produced, please insert --.--.

Column 4, Line 24; after formula, please insert --C--.

Column 4, Line 26; after formula, please insert --C'--.

Column 4, line 37; after which, delete "10".

Column 4, line 45; after 1 to, please delete "10" and substitute therefor --100--.

UNITED STATES PATENT AND TRADEMARK OFFICE

CERTIFICATE OF CORRECTION

PATENT NO. : 5,239,117

DATED : August 24, 1993

INVENTOR(S) : Kenneth M. Nicholas, et al.

It is certified that error appears in the above-indentified patent and that said Letters Patent is hereby corrected as shown below:

Column 6, line 12, in the formula after "Rh), delete "$^{30}$" and substitute therefore --$^{+}$--.

Signed and Sealed this

Ninth Day of August, 1994

Attest:

BRUCE LEHMAN

Attesting Officer

*Commissioner of Patents and Trademarks*